US005540734A

United States Patent [19]
Zabara

[11] Patent Number: 5,540,734
[45] Date of Patent: Jul. 30, 1996

[54] CRANIAL NERVE STIMULATION TREATMENTS USING NEUROCYBERNETIC PROSTHESIS

[76] Inventor: Jacob Zabara, 200 Locust, Apt. 22D, Philadelphia, Pa. 19106

[21] Appl. No.: 314,173

[22] Filed: Sep. 28, 1994

[51] Int. Cl.$^6$ ........................................... A61N 1/32
[52] U.S. Cl. .................. 607/46; 607/48; 607/45; 607/72; 607/118; 600/26
[58] Field of Search .................. 607/44–48, 58, 607/62, 70, 72, 116, 118; 600/26

[56] References Cited

U.S. PATENT DOCUMENTS

| | | |
|---|---|---|
| 3,650,277 | 3/1972 | Sjostrand et al. . |
| 4,174,706 | 11/1979 | Jankelson et al. ........................ 607/62 |
| 4,503,863 | 3/1985 | Katims ................................ 607/62 X |
| 4,573,481 | 3/1986 | Bullara . |
| 4,702,254 | 10/1987 | Zabara . |
| 4,867,164 | 9/1989 | Zabara . |
| 5,025,807 | 6/1991 | Zabara . |
| 5,188,104 | 2/1993 | Wernicke et al. . |
| 5,215,086 | 6/1993 | Terry, Jr. et al. . |
| 5,231,988 | 8/1993 | Wernicke et al. . |
| 5,263,480 | 11/1993 | Wernicke et al. ........................ 607/118 |
| 5,269,303 | 12/1993 | Wernicke et al. ........................ 607/45 |
| 5,299,569 | 4/1994 | Wernicke et al. ........................ 607/45 |
| 5,330,515 | 7/1994 | Rutecki et al. ........................ 607/46 |
| 5,335,657 | 8/1994 | Terry, Jr. et al. ........................ 607/45 |

FOREIGN PATENT DOCUMENTS 1103864   7/1984   U.S.S.R. ................................ 607/45

OTHER PUBLICATIONS

V. Parsonnet et al., "Radio–Frequency Stimulation of the Carotid Baroreceptors in the Treatment of Hypertension", *Surgical Forum* (1966) vol. XVII, Chapter V, pp. 125–127.
B. A. Meyerson et al., "Suppression of Pain in Trigeminal Neuropathy by Electrical Stimulation of the Gasserian Ganglion" *Neurosurgery* 18(1) (1986), pp. 59–66.
A. Neistadt et al., "Implantable Carotid Sinus Nerve Stimulator for Reversal of Hypertension" *Surgical Forum* (1966) vol. XVII, Chapter V, pp. 123–124.
C. Farrchi, "Stimulation of the Carotid Sinus Nerve in Treatment of Angina Pectoris", *American Heart Journal* 80(6) (1970) pp. 759–765.
A. S. Ghea et al., "Bilateral Carotid Nerve Stimulation in the Treatment of Angina Pectoris", *Angiology* 25 (1974) pp. 16–20.
T. K. Peters et al., "The Principle of Electrical Carotid Sinus Nerve Stimulation: A Nerve Pacemaker System for Angina Pectoris and Hypertension Therapy" *Annals of Biomedical Engineering* 8(4–6) (1980), pp. 445–458.
S. Donoghue et al., "Post–Synaptic Activity Evoked in the Nucleus Tractus Solitarius by Carotid Sinus and Aortic Nerve Afferents in the Cat" *J. Physiol.* 360 (1985), pp. 261–273.

*Primary Examiner*—William E. Kamm
*Assistant Examiner*—Jeffrey R. Jastrzab
*Attorney, Agent, or Firm*—Panitch Schwarze Jacobs & Nadel, P.C.

[57] ABSTRACT

The treatment, control or prevention of medical, psychiatric or neurological disorders may be accomplished by application of modulating electric signals to one or both of a patient's trigeminal and glossopharyngeal nerves. The disorders treatable, controllable or preventable by such nerve stimulation include voluntary and involuntary disorders, migraine, epileptic seizure, motor disorders, Parkinson's disease, cerebral palsy, spasticity, chronic nervous illnesses and involuntary movement; pancreatic endocrine disorders including diabetes and hypoglycemia; dementia including cortical, subcortical, multi-infarct, Alzheimer's disease and Pick's disease; sleep disorders including central sleep apnea, insomnia and hypersomnia; eating disorders including anorexia nervosa, bulimia and compulsive overeating; and neuropsychiatric disorders including schizophrenia, depression and borderline personality disorder.

13 Claims, 2 Drawing Sheets

CRANIAL NERVE STIMULATION TREATMENTS USING NEUROCYBERNETIC PROSTHESIS

FIELD OF THE INVENTION

The present invention generally relates to methods for treating, controlling or preventing medical, psychiatric or neurological disorders by application of modulating electrical signals to a selected nerve or nerve bundle of a patient, and more particularly to techniques for treating patients with migraine, epileptic seizures, involuntary motor disorders, chronic nervous illnesses, pancreatic endocrine disorders, dementia, eating disorders and neuropsychiatric disorders.

BACKGROUND OF THE INVENTION

Methods and apparatus for treating or controlling medical, psychiatric or neurological disorders by application of modulating electrical signals to a selected nerve or nerve bundle of the patient, are recognized in the art. The majority of these techniques stimulate one or more nerves which terminate on the target tissue. For example, it is known to stimulate the phrenic nerve, which terminates on the diaphragm, to effect respiration. There are relatively few reports of methods and apparatus which function to stimulate the brain and thereby cause the brain to send signals to the target tissue. The prior art directed to this latter approach to treat or control medical, psychiatric or neurological disorders is directed to the application of electric signals to the vagus and carotid sinus nerves, using an implantable or external neurostimulating device.

The use of nerve stimulation to treat endocrine disorders is disclosed in U.S. Pat. No. 5,231,988, which states that electrical stimulation of the vagus nerve can treat the pancreatic disorders of hypoglycemia and diabetes mellitus.

The use of nerve stimulation to treat and control migraine is disclosed in U.S. Pat. No. 5,215,086, which states that selective modulation of vagus nerve electrical activity can treat migraine symptoms.

The use of a neurocybernetic prosthesis, including a pulse generator which generates electrical pulses, to control or prevent epileptic seizures, as well as treat various involuntary movements, is disclosed in U.S. Pat. Nos. 5,025,807, 4,867,164 and 4,702,254. These patents disclose electrical stimulation of the vagus nerve to treat involuntary movement disorders.

U.S. Pat. No. 5,269,303 discloses the application of an electrical stimulating signal to the vagus nerve to treat symptoms of dementia, including cortical dementia, subcortical dementia and multi-infarct dementia.

The selective stimulation of the vagus nerve to treat and control eating disorders in general and compulsive eating disorders in particular is disclosed in U.S. Pat. Nos. 5,188,104 and 5,263,480, which disclose electric stimulation of the vagus nerve as a means of treating obesity, bulimia or anorexia nervosa.

U.S. Pat. No. 5,330,515 discloses electrical stimulation of the vagus nerve to treat pain.

U.S. Pat. No. 5,335,657 discloses electrical stimulation of the vagus nerve to treat sleep disorders.

U.S. Pat. No. 5,299,569 discloses a method and apparatus for treating and controlling neuropsychiatric disorders including schizophrenia, depression and borderline personality disorder by selectively applying a predetermined electrical signal to a patient's vagus nerve.

A. Neistadt and S. I. Schwartz in "Implantable Carotid Sinus Nerve Stimulator For Reversal of Hypertension" *Surgical Forum* Volume XVII, Proceedings of the 22nd Annual Session of the Forum on Fundamental Surgical Problems, 52nd Clinical Congress of the American College of Surgeons, San Francisco, Calif., October 1966, Chapter V: Cardiovascular Problems, pp. 123–124, disclose an implantable carotid sinus nerve stimulator for reversal of hypertension.

V. Parsonnet; G. H. Myers; W. G. Holcomb and I. R. Zucker in "Radio-Frequency Stimulation of the Carotid Baroreceptors in the Treatment of Hypertension" *Surgical Forum supra*, pp. 125–127, disclose that radiofrequency radiation used to stimulate a carotid baroreceptor was found to lower the systemic arterial blood pressure in dogs, but that responsiveness was lost in long-term nerve stimulation.

T. K. Peters, H. E. Koralewski and E. Zerbst in "The Principle of Electrical Carotid Sinus Nerve Stimulation: A Nerve Pacemaker System for Angina Pectoris and Hypertension Therapy" *Annals of Biomedical Engineering* 8(4–6):445–458 (1980) disclose a closed loop nerve pacemaker system for electrical carotid sinus nerve stimulation.

C. Farrchi in "Stimulation of the Carotid Sinus Nerve in Treatment of Angina Pectoris" *American Heart Journal* 80(6):759–765 (1970) discloses effects of implanting and using a carotid sinus nerve stimulator to alleviate attacks of angina. Farrchi states that the treatment is not intended to affect the glossopharyngeal nerve.

A. S. Geha, R. E. Kleiger and A. E. Baue in "Bilateral Carotid Nerve Stimulation in the Treatment of Angina Pectoris" *Angiology* 25:16–20 (1974) disclose the bilateral stimulation of the carotid nerve to treat angina pectoris.

B. A. Meyerson and S. Håkanson in "Suppression of Pain in Trigeminal Neuropathy by Electrical Stimulation of the Gasserian Ganglion" *Neurosurgery* 18(1):59–66 (January, 1966) disclose pain treatment by direct electrical stimulation of the trigeminal ganglion and rootlets via an implanted electrode.

S. Donoghue, R. B. Relder, M. P. Gilbery, D. Jordan and K. M. Spyer in "Post-Synaptic Activity Evoked in the Nucleus Tractus Solitarius by Carotid Sinus and Aortic Nerve Afferents in the Cat" *J. Physiol.* 360:261–273 (1985) disclose the electrical stimulation of the carotid sinus, aortic and vagal nerves, alone or in combination, and discuss the significance of their studies on determining the role of the nucleus tractus solitarius in cardiorespiratory reflexes.

U.S. Pat. No. 3,650,277 discloses a system for reducing and controlling the blood pressure of a hypertensive patient by electrical pulse stimulation of the carotid sinus nerves, and in particular, stimulation of an afferent nerve from a baroreceptor in an individual.

U.S. Pat. No. 4,573,481 discloses an implantable helical electrode assembly configured to fit around a nerve for electrically triggering or measuring an action potential or for blocking conduction in nerve tissue.

In general, the prior art recognizes that electrical stimulation of a patient's vagus nerve may provide beneficial effect to a patient receiving such treatment. It is also known that electrical stimulation of the carotid sinus nerve, which is a branch of the glossopharyngeal nerve, may provide therapeutic treatment to patients suffering from hypertension and angina pectoris.

SUMMARY OF THE INVENTION

The invention is directed to methods of treating, controlling or preventing medical, psychiatric or neurological disorders by application of modulating electric signals directly to at least one of a patient's trigeminal and glossopharyngeal nerves. The disorders treatable, controllable or preventable by the methods of the invention are selected from the group consisting of voluntary and involuntary disorders, migraine, epileptic seizure, Parkinson's disease, cerebral palsy, spasticity, involuntary movement and chronic nervous illnesses; pancreatic endocrine disorders including diabetes and hypoglycemia; dementia including cortical, subcortical, multi-infarct, Alzheimer's disease, and Pick's disease; eating disorders including anorexia nervosa, bulimia, and compulsive overeating; neuropsychiatric disorders including schizophrenia, depression and borderline personality disorder, and sleeping disorders.

BRIEF DESCRIPTION OF THE DRAWINGS

The foregoing summary, as well as the following detailed description of the preferred embodiment of the invention, will be better understood when read in conjunction with the appended drawings. For the purpose of illustrating the invention, there is shown in the drawing an embodiment which is presently preferred. It should be understood, however, that the invention is not limited to the precise arrangements and instrumentalities shown. In the drawings.

DETAILED DESCRIPTION OF PREFERRED EMBODIMENTS

The central nervous system contains the following cranial nerves: olfactory, optic, oculomotor, trochlear, trigeminal, abducens, facial, vestibuloccochlear, glossopharyngeal, vagus, accessory and hypoglossal nerves. The carotid sinus nerve is a branch of the glossopharyngeal nerve. According to the present invention, electrical stimulation of one or both of the trigeminal or glossopharyngeal nerves is provided as a means to treat, control or prevent medical, psychiatric or neurological disorders, as discussed below. The present method acts to stimulate nerve afferents which in turn stimulate the brain and cause/allow the brain to act in the best interest of the host through use of the brain's natural mechanisms. The prior art fails to recognize that stimulation of at least one of a patient's glossopharyngeal and trigeminal nerves can provide the therapeutic treatments according to the instant invention.

It may come as a surprise to one skilled in the art to learn that stimulation of at least one of a patient's glossopharyngeal and trigeminal nerves may be used to treat the maladies disclosed herein. The trigeminal nerve subserves pain, temperature, pressure in the mouth, taste buds on the tongue, and controls some movement of the jaw. The glossopharyngeal nerve is involved in the feedback for blood pressure, and subserves, for example, gagging. While the normal functions of the trigeminal and glossopharyngeal nerves would not suggest to one skilled in the art that they could be used to treat, for example, the voluntary and involuntary muscle disorders disclosed herein, these two nerves have qualities which make them suited for the method of the invention.

For example, both the glossopharyngeal and trigeminal nerves are cranial nerves, being part of the parasympathetic nervous system, and thus have afferents which terminate directly in the brain. Also, both the glossopharyngeal and trigeminal nerves have a relatively large number of afferents going to the brain, which is not the case for some other cranial nerves, e.g., the oculomotor. As the number of stimulated afferents going to the brain increases, there is a greater opportunity for a stimulated afferent to terminate at a pathway leading from the brain to the target tissue. Also, neither of these two nerves will habituate, also known as adapt, i.e., fail to respond to electric stimulation after prolonged stimulation, as is the case for many other nerves.

Figure 1:
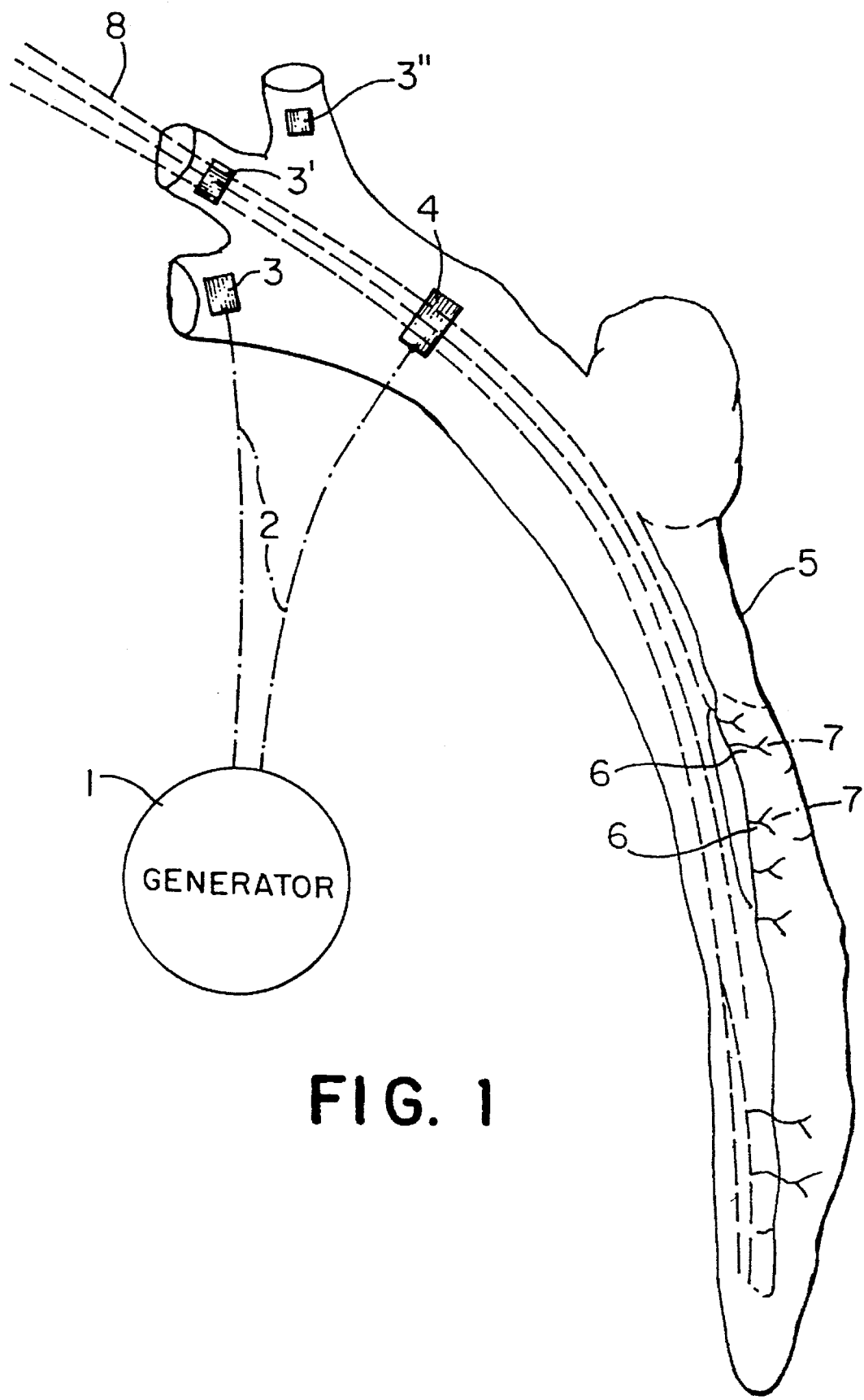
FIG. 1 is a highly simplified, schematic diagram of the trigeminal nerve, showing possible sites of electrode attachment.
Figure 2:
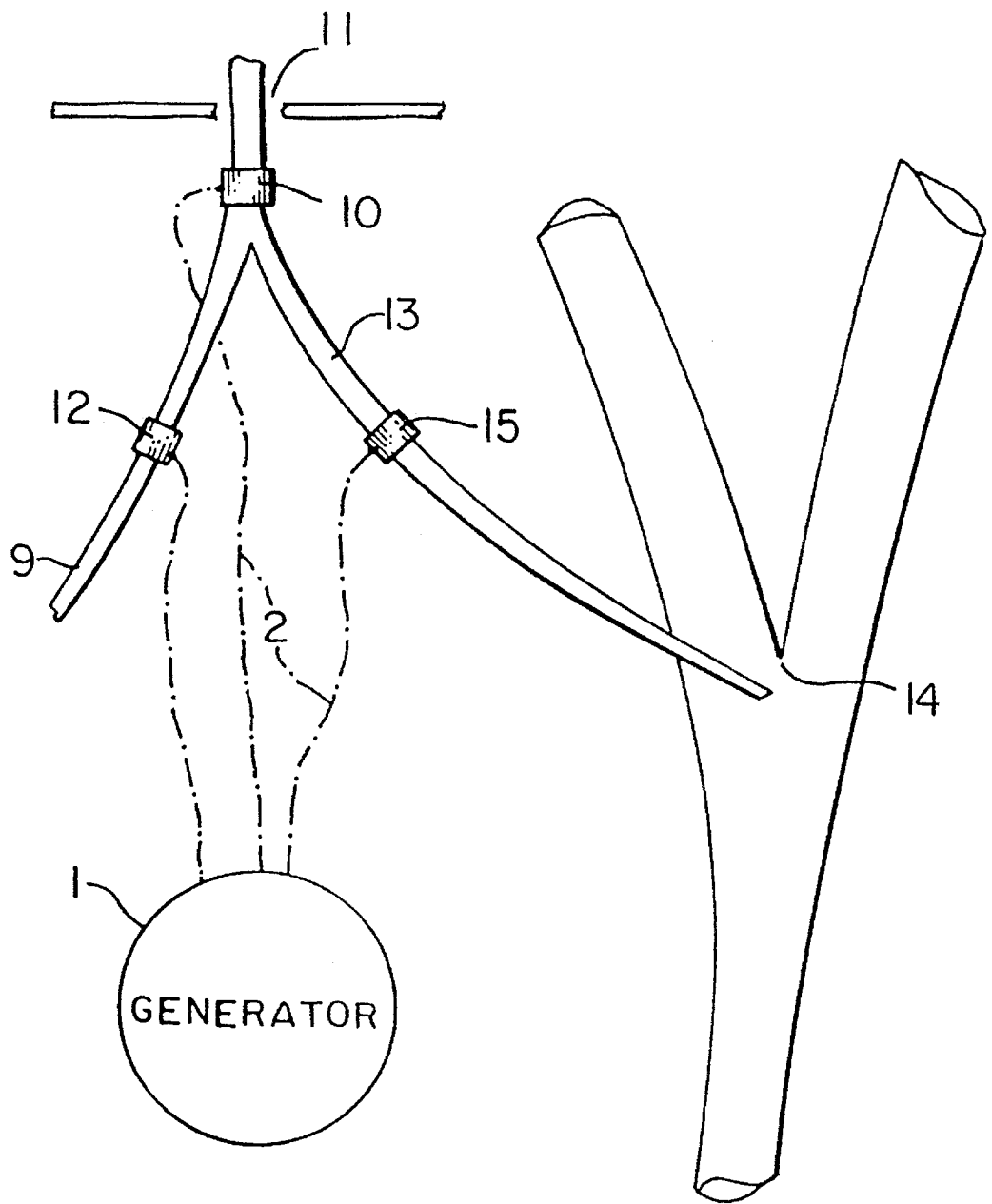
FIG. 2 is a highly simplified, schematic diagram of the glossopharyngeal nerve, showing possible sites of electrode attachment.

The instant invention employs electrodes attached to at least one of the trigeminal or glossopharyngeal nerves, as illustrated in FIGS. 1 and 2.

FIG. 1 illustrates possible sites for attachment of electrodes to the trigeminal nerve. FIG. 1 shows schematically a generator 1, which may be surgically implanted at some point in the patient's body in a known manner. Preferably, the generator 1 is implanted in or near the chest. Extending from the generator 1 are one or more generator leads 2 which terminate at one or more electrodes, preferably helical electrodes, placed on the trigeminal nerve 8, shown as three nerve fibers. Recommended sites for electrode placement are shown at 3, 3' and 3", which are the three nerve roots of the trigeminal nerve. Another recommended site is the gasserian ganglion, identified as 4 in FIG. 1. Also shown schematically in FIG. 1 is the medullary region 5 of the brain, with primary nerve endings 6 of the trigeminal nerve, and where 7 indicates pathway projections in the brain leading away from the nerve endings 6.

It should be possible to selectively stimulate the fibers of the opthalamic, maxillary or mandibular branches of the trigeminal nerve. The sensation elicited by selective stimulation can demonstrate which group of fibers is being stimulated. Tactile and pressure fibers terminating in the trigeminal nucleus give rise to touch and pressure sensations. Pain and temperature fibers terminate in the trigeminal nucleus and give rise to cold, heat and pain sensations. In addition, the stimulated fibers can be monitored in more detail by observing in which part of the face the sensation arises.

FIG. 2 illustrates possible sites for attachment of electrodes to the glossopharyngeal nerve. FIG. 2 shows schematically a generator 1, which may be surgically implanted at some point in the patient's body in a known manner. Preferably, the generator 1 is implanted in or near the chest. Extending from the generator 1 are one or more generator leads 2 which terminate at one or more electrodes, preferably helical electrodes, placed on the glossopharyngeal nerve 9. Recommended sites for electrode placement include site 10, which is where the glossopharyngeal nerve enters the brain through the jugular foramen 11. Alternatively or additionally, an electrode may be placed on the glossopharyngeal nerve at a point distal from the jugular foramen, as indicated, for example, by electrode placement site 12. One point distal from the jugular foramen is along the carotid sinus 13, which connects to the bifurcation of the carotid artery 14. It may be convenient for a surgeon to locate an electrode at placement site 15 on the carotid sinus, or an electrode placement site 10 just outside the jugular foramen, by first locating the bifurcation in the carotid artery 14, and tracing the glossopharyngeal nerve from that point.

The instant invention provides for the treatment and control of endocrine disorders, including diabetes and other systemic pancreatic endocrine disorders attributable to abnormal levels of secretion of endogenous insulin. According to the method, a generator, also known as an electrical stimulator or simply stimulator, is implanted into, or worn external to the patient's body. The stimulator is adapted so that, when activated, it generates a programmable electrical waveform for application to electrodes implanted on at least one of the trigeminal and glossopharyngeal nerves of the patient. The electrical waveform is programmed using parameter values selected to stimulate or inhibit said nerves to modulate the electrical activity thereof and thereby increase or decrease secretion of natural insulin by the patient's pancreas.

The stimulator may be selectively activated manually by the patient in response to direct measurement of blood glucose or symptoms, or activated automatically by programming the activation to occur at predetermined times and for predetermined intervals during the circadian cycle of the patient. Alternatively, the automatic activation is achieved using an implanted sensor to detect the blood glucose concentration, and is triggered when the patient's blood glucose concentration exceeds or falls below a predetermined level depending on whether diabetes or hypoglycemia is being treated. U.S. Pat. No. 5,231,988 discloses techniques and devices which may be adapted for use in the instant invention. The entire disclosure of U.S. Pat. No. 5,231,988 is incorporated herein by reference.

The instant invention also provides for the treatment of compulsive eating disorders, including bulimia, anorexia nervosa and compulsive overeating/obesity, by electrical stimulation of at least one of a patient's t&g nerves. According to the instant invention, a means is provided for detecting a preselected event indicative of an imminent need for treatment of the specific eating disorder of interest, and responding to the detected occurrence of the preselected event by applying a predetermined stimulating signal to at least one of the patient's trigeminal and glossopharyngeal nerves to alleviate the effect of the eating disorder.

Suitable means for detecting the preselected event indicative of an imminent need for treatment are disclosed in U.S. Pat. Nos. 5,188,104 and 5,263,480, the entire disclosures of which are incorporated herein by reference. The preselected event may be a specified level of food consumption by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to at least one of the trigeminal and glossopharyngeal nerves.

In cases where the disorder is compulsive overeating to excess, the stimulating signal is predetermined to produce a sensation of satiety in the patient. The occurrence of the preselected event is determined by summing the number of swallows of food by the patient within the set interval of time. In cases where the disorder is compulsive refusal to eat (anorexia nervosa), the stimulating signal is predetermined to produce a sensation of hunger or to suppress satiety in the patient.

The instant invention also provides for the treatment of dementia, including cortical dementia, subcortical dementia and multiinfarct dementia, where cortical dementia includes Alzheimer's disease and Pick's disease, and where subcortical dementia includes Parkinson's disease, Huntington's chorea and supranuclear palsy. The treatment of the invention comprises application of an electrical signal to at least one of the patient's trigeminal and glossopharyngeal nerves. According to a preferred embodiment, said signal is generated in response to certain patterns in a patient's EEG signal. Suitable means to monitor a patient's EEG, as well as suitable signal levels, frequencies, amplitudes and voltages for the stimulating signal are described in U.S. Pat. No. 5,269,303, the entire disclosure of which is incorporated herein by reference.

The instant invention also provides for the control or prevention of epileptic seizures and other motor disorders. According to the invention, electrodes are directed to a patient's trigeminal and/or glossopharyngeal nerves in a manner analogous to that described in U.S. Pat. Nos. 4,702,254, 4,867,164 and 5,025,807, the disclosures of which are incorporated herein by reference. The '254, '164 and '807 patents teach the stimulation of the vagus nerve, rather than the trigeminal or glossopharyngeal nerves, but in all other respects these three patents provide appropriate techniques and devices amenable to the practice of the instant invention.

The present invention is also directed to the treatment and control of migraine by selectively applying a predetermined electrical signal to at least one of a patient's trigeminal and glossopharyngeal nerves. The signal is a pulse waveform having parameters programmed to desynchronize the patient's EEG as paroxysmal activity is detected in the EEG, or to synchronize the EEG as low voltage fast wave activity is detected. Alternatively, the application of the stimulating signal to the trigeminal and glossopharyngeal nerve may be initiated manually by the patient upon recognition of the onset of a migraine attack. The signal to the trigeminal and glossopharyngeal nerve is generated by a neurostimulator device, which is preferably implanted in the patient as disclosed in the '086 patent, where said device has a power down circuit to conserve battery power.

The present invention is also directed to a method for treating and controlling neuropsychiatric disorders, including schizophrenia, depression and borderline personality disorder, by selectively applying a predetermined electrical signal to at least one of a patient's trigeminal and glossopharyngeal nerves for stimulation thereof to alleviate the symptoms of the disorder being treated. The electrical signal may be applied continuously, periodically, or intermittently to at least one of said nerves depending, in part, on the symptoms of the disorder being treated.

In certain instances, the electrical signal is applied upon detection of an event indicative of onset of the neuropsychiatric disorder, as described in U.S. Pat. No. 5,299,569, the entire disclosure of which is incorporated herein by reference. In other instances, and as also described in the '569 patent, the electrical signal is applied at will to at least one of the trigeminal and glossopharyngeal nerves, such as by patient activation of the signal generator. Parameter values of the electrical signal include pulse width, output current, frequency, on time and off time, and are programmed according to values given in the '569 patent.

The present invention is also directed to a method for treating and controlling sleep disorders, wherein the sleep disorder may be identified, for example, by sensing a patient's EEG activity in the case of insomniac and hypersomniac patients, or detecting sudden nodding of the head in the case of narcoleptic patients, or sensing the cessation of respiration in the case of sleep apnea patients. The method according to the invention detects the sleep disorder under treatment, and, in response, selectively applies a predetermined electrical signal to at least one of the patient's trigeminal and glossopharyngeal nerves, for the stimulation thereof to alleviate the sleep disorder under treatment. The method of treatment is analogous to that described in U.S. Pat. No. 5,335,657, the entire disclosure of which is incorporated herein by reference, and is applicable to central sleep apnea, insomnia, hypersomnia, sleep walking, enuresis and symptoms thereof.

The preferred implantable neurostimulator of the invention is described in detail in U.S. Pat. No. 5,154,172, the entire disclosure of which is incorporated herein by reference. While it is typically preferred to have the neurostimulator device implanted into the patient, an external device may also be used. A suitable implantable neurostimulator, also known as a generator, may be obtained from Cyberonics, Inc. of Webster, Texas as Model 100 NCP Pulse Generator.

The trigeminal nerve may be stimulated either proximal or distal to the trigeminal ganglion by a helical or patch electrode. A suitable electrode is a helical electrode, disclosed, for example, in U.S. Pat. Nos. 4,573,481 and 5,154,172. Preferably, the diameter of the helical electrode should be about equal to or somewhat larger than the diameter of the nerve being stimulated by the electrode.

The quality of the stimulation of at least one of the trigeminal and glossopharyngeal nerves is important in achieving the desired effects. One wants to stimulate the trigeminal and/or glossopharyngeal nerves in such a way that the brain responds in the desired manner. There are several variables of the stimulation which may and should be controlled by a caregiver, and optimized in order to obtain the maximum treating or controlling effect for the malady under treatment. The optimization of the various variables, which will be discussed below, will need to be determined for each individual receiving the treatment, as there will likely be variability in the responses of the patients to the stimulation.

One variable which should be considered first is whether one or both of the glossopharyngeal or trigeminal nerves will receive stimulation. It is generally true that stimulation of both nerves will provide more stimulation of the brain, and thus more stimulation of pathways leading from the brain. Stimulation of both nerves thus increases the likelihood of reaching the target tissue(s). However, stimulation of both nerves also increases the likelihood of reaching nontarget tissue(s), leading to possible undesirable side-reactions. Factors such as the patient's tolerance to the implanting surgery, etc. will need to be considered by the surgeon in determining the extent of electrode placement.

If both nerves will not receive implants, then one of the two nerves must be selected for implant receipt. The selection will need to be based, in part, on the malady for which the treatment is intended. As the trigeminal nerve generally has a broader range of function, it will typically be more useful in the inventive method. The trigeminal nerve, which subserves pain, will typically be preferred for treatment of migraine. The relatively one-dimensional scope of the glossopharyngeal nerve offers the opportunity for being more selective in the brain stimulation.

After selecting the nerve which will receive the implant, one must determine the site at which the implant will be placed. As shown in FIG. 1, the trigeminal nerve has three nerve roots. An electrode may be placed at one or more of these roots. Alternatively, the electrode may be placed at the Gasserian Ganglion, which is a terminus for the three roots. Signals will travel from the Gasserian Ganglion to the Trigeminal Nucleus, and then generate impulses in pathways projecting to other areas of the brain. As shown in FIG. 2, the glossopharyngeal nerve may be accessed just prior to its entry into the brain, which occurs at the jugular foramen. Alternatively, one of the branches of the glossopharyngeal nerve may receive the electrode, including the carotid sinus nerve. The surgeon will often find it convenient to first locate the bifurcation of the carotid artery, and at that point identify the carotid sinus nerve which may be traced to the jugular foramen.

After the nerve(s) have been fitted with electrodes, a stimulation regime must be developed. In general, one can vary the current, frequency, pulse width, period, duration and rate of the electric signals. As used herein, the current of the electric signal refers to how many milliamperes are being delivered, and is typically about 1.0 to 10 milliamperes, but can range from about 0.5 to about 20 milliamperes. As used herein, the frequency of the signal refers to how many cycles per second make up the current, and is typically about 10 to about 30 cycles per second, but can range from about 5 to about 300 cycles per second. As used herein, the pulses width refers to how long a single pulse will last, and can vary between about 0.1 and 1 millisecond. As used herein, the period of stimulation refers to how often a continuous signal is sent to the electrode. For example, a continuous stimulating signal might be sent once a minute, or twice an hour, etc. As used herein, the duration of stimulation refers to how long a single continuous stimulation will last. For example, a stimulating signal might be given for a duration of 10 seconds or 30 seconds. As used herein, the rate of stimulation refers to how many electric pulses are sent to the electrode, every second, to provide a single continuous stimulation. Thus a pulse regime might be for a duration of 30 seconds, provided to the patient with a period of once per hour, using a constant current at 2 milliamperes with a pulse width of 500 microseconds and frequency of 20 cycles per second.

The optimum value of these parameters will depend on the malady being treated and the condition of the patient. The optimization of these parameters can be achieved by what will be termed herein as "spectral optimization". According to spectral optimization, the various parameters associated with the electric pulses are increased in steps over several weekly intervals, and the patient's response is monitored. If discomfort occurs, no further increase in current, pulse width, frequency etc. is attempted, until the discomfort response habituates. If the discomfort does not habituate, the parameters are decreased.

The pulse generator should be capable of generating electric pulses having a frequency of between about 1 and 300 cycles per second, a pulse duration of between about 0.1 and 1 millisecond, and a constant current of between about 1 and 20 milliamperes. A suitable pulse generator and associated software according to the invention is described in U.S. Pat. No. 5,154,172. The change in parameters values is preferably accomplished via a programming wand held over the region of the microcomputer-based pulse generator.

In general, the period of stimulation will be less for the trigeminal nerve than for the glossopharyngeal nerve. For instance, a period of once a week might be sufficient for the glossopharyngeal nerve, but once a day might be preferred for the trigeminal nerve.

The present invention may be embodied in other specific forms without departing from the spirit or essential attributes thereof and, accordingly, reference should be made to the appended claims, rather than to the foregoing specification as indicating the scope of the invention.

I claim:

1. A method of treating, controlling or preventing medical, psychiatric or neurological disorders selected from the group consisting of motor disorders; migraine; chronic nervous illness; pancreatic endocrine disorders including diabetes and hypoglycemia; dementia including cortical, subcortical, multi-infarct, Alzheimer's disease and Pick's disease; eating disorders including anorexia nervosa, bulimia, and compulsive overeating; sleep disorders including insomnia, hypersomnia, narcolepsy and sleep apnea; and neuropsychiatric disorders including schizophrenia, depression and borderline personality disorder, comprising the steps of attaching at least one electrode to afferents of at least one of a patient's trigeminal and glossopharyngeal nerves, and applying modulating electric signals to at least one of the patient's trigeminal and glossopharyngeal nerves through the at least one electrode.

2. The method according to claim 1 wherein the modulating electric signals have a frequency of about 5 to about 300 cycles per second at a constant current of between about 0.5 and about 20 milliamperes, and a pulse width of between about 0.1 and 1 millisecond.

3. The method according to claim 1, wherein patients experiencing symptoms of migraine are treated by a process comprising
   a. detecting a physiological symptom associated with onset of a migraine attack in a patient under treatment, and
   b. in response to detection of such symptom, selectively applying said modulating electric signals as a programmed electrical stimulus to at least one of the patient's trigeminal and glossopharyngeal nerves, for modulating electrical activity of preselected fibers of said nerve, in a manner to alleviate the migraine attack.

4. The method according to claim 1, wherein patients experiencing symptoms of migraine are treated by a process comprising
   a. providing an electrical stimulus generator with an electrical output signal having parameters which are programmable within predetermined ranges, and adapting the stimulus generator to generate its output signal upon selective activation of the stimulus generator,
   b. implanting the stimulus generator in the patient's body, and implanting a nerve electrode to receive the output signal of the stimulus generator on at least one of the trigeminal and glossopharyngeal nerves of the patient, and
   c. programming at least some of the programmable parameters of the output signal of the stimulus generator according to the symptoms of the migraine suffered by the particular patient under treatment to modulate electrical activity of said nerve in a predetermined manner, upon activation of the stimulus generator and
   d. applying said modulating electric signals as the programmed output signal to said nerve through the nerve electrode planted thereon, to alleviate symptoms of a migraine episode experienced by the patient.

5. The method according to claim 1 wherein the motor disorder is a seizure associated with epilepsy, Parkinson's disease, cerebral palsy and chronic nervous illnesses, and wherein said electric signals are applied repeatedly over a period of time to thereby prevent or control such seizures.

6. The method according to claim 1 wherein involuntary movements due to epileptic seizures, cerebral palsy, Parkinson's disease, and spasticity are controlled or prevented, further comprising the step of determining that an involuntary movement is going to occur and thereafter applying said modulating electric signals as a pulsed electrical signal to at least one of the trigeminal and glossopharyngeal nerves to thereby prevent such movement.

7. The method according to claim 1, comprising treating pancreatic endocrine disorders, diabetes and hypoglycemia including the steps of:
   (a) detecting a blood glucose concentration indicative of an endocrine disorder in a patient, and
   (b) in response to such detection, selectively applying said modulating electric signals to at least one of the patient's trigeminal and glossopharyngeal nerves for modulation of electrical activity thereof, to adjust secretion of endogenous insulin and thereby control the endocrine disorder.

8. The method according to claim 1, comprising treating and controlling diabetes in a patient including the steps of:
   (a) providing a programmable device responsive, when activated, to apply said modulating electric signals as a programmed electrical signal to at least one of the patient's trigeminal and glossopharyngeal nerves for stimulation thereof to adjust secretion of endogenous insulin appropriate to maintain insulin-glucose homeostasis in the patient's bloodstream and thereby control the diabetes, and
   (b) periodically activating the device to maintain the homeostasis.

9. The method according to claim 1, comprising treatment of patients with dementia, including cortical dementia, subcortical dementia, multi-infarct dementia, Alzheimer's disease, Pick's disease and vascular dementia, including the steps of:
   (a) selecting a patient suffering from dementia, and
   (b) applying said modulating electric signals with predetermined electrical parameters to at least one of the patient's trigeminal and glossopharyngeal nerves to selectively modulate electrical activity of preselected afferent fibers of said nerve distributed to a reticular activating system in a patient's brain stem and thereby modulate the electrical activity of preselected portions of the reticular activating system of the patient, to relieve a symptom of the dementia.

10. The method according to claim 1 comprising treating and controlling the symptoms of dementia, including cortical dementia, subcortical dementia, multi-infarct dementia, Alzheimer's disease, Pick's disease and vascular dementia, in a patient, comprising the steps of:
    (a) selecting a patient suffering from dementia,
    (b) implanting an electrode on at least one of the patient's trigeminal and glossopharyngeal nerves for application of an electrical signal having predetermined electrical parameter values to the nerve accepting the implant, and
    (c) delivering the modulating electrical signals to the implanted electrode to selectively modulate electrical activity of said nerve and thereby treat a symptom of the dementia exhibited by the patient.

11. The method according to claim 1, comprising the treatment of patients with an eating disorder, including anorexia nervosa, bulimia and compulsive overeating, by therapy which alleviates a symptom of the disorder and includes the steps of:
    (a) detecting a preselected event indicative of an imminent need for treatment of a specific eating disorder, and (b) responding to a detected occurrence of the preselected event by applying said modulating electric signals to at least one of the patient's trigeminal and glossopharyngeal nerves appropriate to alleviate said symptom of the eating disorder.

12. The method according to claim 1, comprising treatment of patients with neuropsychiatric disorders, including schizophrenia, depression and borderline personality disorder, including (a) determining symptoms of a neuropsychiatric disorder being exhibited by the patient, (b) selectively applying said modulating electric signals to at least one of the patient's trigeminal and glossopharyngeal nerves for modulating electrical activity thereof in a manner to alleviate symptoms of the neuropsychiatric disorder exhibited by the patient being treated.

13. The method according to claim 1, comprising treatment Of patients experiencing sleep disorders, which includes the step of:

(a) detecting a physiological event associated with the sleep disorder in the patient to be treated, and (b) upon detection of such physiological event, applying said modulating electric signals to at least one of the patient's trigeminal and glossopharyngeal nerves for modulating the electrical activity of said nerve to alleviate the sleep disorder under treatment.

* * * * *